United States Patent [19]

Davies et al.

[11] 4,302,460
[45] Nov. 24, 1981

[54] 4-QUINOLINONES HAVING ANTIHYPERTENSIVE ACTIVITY

[75] Inventors: Roy V. Davies, Sutton-in-Ashfield; James Fraser; Kenneth J. Nichol, both of Nottingham; Raymond Parkinson, Lowdham; Malcolm F. Sim, Woodborough; David B. Yates, Farnsfield, all of England

[73] Assignee: The Boots Company Limited, Nottingham, England

[21] Appl. No.: 133,310

[22] Filed: Mar. 24, 1980

[30] Foreign Application Priority Data

Mar. 27, 1979 [GB] United Kingdom ............... 10558/79
Nov. 15, 1979 [GB] United Kingdom ............... 39505/79

[51] Int. Cl.$^3$ .................... A61K 31/47; C07D 215/36
[52] U.S. Cl. .................... 424/258; 546/155; 560/11; 560/16; 564/440
[58] Field of Search .................... 546/155; 424/258

[56] References Cited

U.S. PATENT DOCUMENTS

| | | | |
|---|---|---|---|
| 3,178,348 | 4/1965 | Bickerton | 424/258 |
| 3,652,571 | 3/1972 | Sturm et al. | 546/155 |
| 3,772,301 | 11/1973 | von Strandtmann et al. | 424/258 X |
| 3,798,219 | 3/1974 | von Strandtmann et al. | 424/250 X |
| 4,017,629 | 4/1977 | Habicht et al. | 424/266 |
| 4,124,587 | 11/1978 | Hardtmann | 546/90 |
| 4,127,574 | 11/1978 | Hardtmann et al. | 546/90 |
| 4,177,278 | 12/1979 | Bossert et al. | 424/266 |
| 4,188,395 | 2/1980 | Bossert et al. | 424/266 |
| 4,198,512 | 4/1980 | Kubo et al. | 546/142 |

FOREIGN PATENT DOCUMENTS

| | | |
|---|---|---|
| 858279 | 2/1978 | Belgium . |
| 862107 | 6/1978 | Belgium . |
| 865658 | 10/1978 | Belgium . |
| 2616991 | 10/1977 | Fed. Rep. of Germany . |
| 2616995 | 10/1977 | Fed. Rep. of Germany . |
| 2639257 | 3/1978 | Fed. Rep. of Germany . |
| 2641746 | 3/1978 | Fed. Rep. of Germany . |
| 2658804 | 7/1978 | Fed. Rep. of Germany . |
| 2747513 | 5/1979 | Fed. Rep. of Germany . |
| 1066917 | 4/1967 | United Kingdom . |
| 2002365 | 2/1979 | United Kingdom . |

OTHER PUBLICATIONS

Coppala, et al., J. Heterocyclic Chem., vol. 16, pp. 1605–1610 (1979).
van Leusen, et al., J. Org. Chem., vol. 33, pp. 66–70 (1968).
Wright, et al., J. Med. Chem., vol. 14, No. 11, pp. 1060–1066 (1971).
Böhme, et al., Archiv der Pharmaz., vol. 305, pp. 93–96 (1972).
Albrecht, Chimie Therapeutique, 1973, No. 1, pp. 45–48.
Yanagisawa, et al., Chem. Pharm. Bull., vol. 21, No. 5, pp. 1080–1089 (1973).
Coppala, et al., J. Org. Chem., vol. 41, pp. 825–831 (1976).
Connor, et al., J. Heterocyclic Chem., vol. 15, pp. 113–114 (1970).
Connor, et al., J. Heterocyclic Chem., vol. 15, pp. 115–117 (1978).

Primary Examiner—Donald G. Daus
Assistant Examiner—Diana G. Rivers
Attorney, Agent, or Firm—Gordon W. Hueschen

[57] ABSTRACT

Compositions which contain a quinolone compound of the general formula

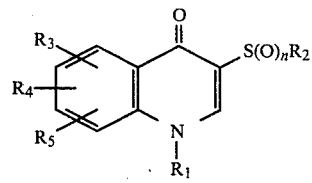

wherein n is 0, 1 or 2; $R_1$ is lower alkyl optionally substituted by hydroxy or $C_{1-4}$ alkoxycarbonyl; allyl; propynyl or phenyl- lower alkyl in which the phenyl ring is optionally substituted by 1 or 2 $C_{1-4}$ alkoxy groups; $R_2$ is $C_{1-4}$ alkyl with the proviso that when n is 0, $R_2$ is methyl; and $R_3$, $R_4$ and $R_5$, which may be the same or different, are hydrogen, lower alkyl, lower alkoxy, lower alkanoyl, halo, trifluoromethyl or lower alkylthio show antihypertensive activity.

Compounds of general formula

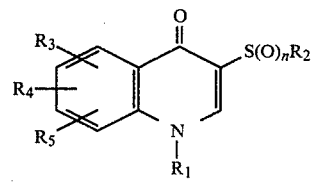

in which n, $R_1$ $R_2$, $R_3$, $R_4$ and $R_5$ are as described above are novel subject to the following provisos (a) when $R_3$, $R_4$ and $R_4$ and $R_5$ are hydrogen $R_2$ is methyl and $R_1$ is lower alkyl, $R_1$ contains more than one carbon atom, and (b) when $R_3$ and $R_4$ are hydrogen, $R_5$ is hydrogen or 7-methyl, and $R_1$ is ethyl, $R_2$ contains more than one carbon atom.

The specification describes and claims methods of making the compounds and novel intermediates used in such methods.

43 Claims, No Drawings

4-QUINOLINONES HAVING ANTIHYPERTENSIVE ACTIVITY

This invention relates to quinolone compounds with therapeutic activity and to therapeutic compositions containing such compounds. More particularly, the present invention relates to quinolone compounds of the general formula

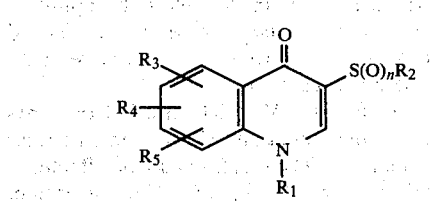

wherein n is 0, 1 or 2; $R_1$ is lower alkyl optionally substituted by hydroxy or $C_{1-4}$ alkoxycarbonyl; allyl; propynyl or phenyl-lower alkyl in which the phenyl ring is optionally substituted by 1 or 2 $C_{1-4}$ alkoxy groups; $R_2$ is $C_{1-4}$ alkyl with the proviso that when n is 0, $R_2$ is methyl; and $R_3$, $R_4$ and $R_5$, which may be the same or different, are hydrogen, lower alkyl, lower alkoxy, lower alkanoyl, halo, trifluoromethyl or lower alkylthio.

We have found that the compounds of general formula I have valuable antihypertensive activity. When administered to warm blooded animals in non-toxic doses the compounds are effective in reducing elevated blood pressure. Thus the present invention provides therapeutic compositions which comprise a quinolone compound of the formula I together with a pharmaceutically acceptable carrier.

Many of the compounds of formula I are novel. The present invention provides novel compounds of general formula I as hereinbefore defined with the further provisos that (a) when $R_3$, $R_4$ and $R_5$ are hydrogen $R_2$ is methyl and $R_1$ is lower alkyl, $R_1$ contains more than one carbon atom, and (b) when $R_3$ and $R_4$ are hydrogen, $R_5$ is hydrogen or 7-methyl, and $R_1$ is ethyl, $R_2$ contains more than one carbon atom.

The terms "lower alkyl", "lower alkoxy", "lower alkanoyl", and "lower alkylthio" denote such groups containing 1–8 carbon atoms, especially 2–4 carbon atoms for lower alkanoyl and 1–4 carbon atoms for the other groups. Examples of such groups include methyl, ethyl, propyl, isopropyl, n-butyl, isobutyl, tert-butyl, n-heptyl, n-octyl, methoxy, ethoxy, propoxy, n-butoxy, isobutoxy, acetyl, propionyl, butyryl, methylthio, ethylthio, propylthio and n-butylthio.

As used hereinafter, the term 'active compound' denotes a quinolone compound of general formula I. In therapeutic use, the active compound may be administered orally, rectally or parenterally, preferably orally. Thus the therapeutic compositions of the present invention may take the form of any of the known pharmaceutical compositions for oral, rectal or parenteral administration. Pharmaceutically acceptable carriers suitable for use in such compositions are well known in the art of pharmacy. The compositions of the invention suitable contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The exipients used in the preparation of these compounds are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added exipients, may be prepared by conventional means and, if desired, provided with enteric coatings in a known manner. The tablets and capsules may conveniently each contain 5–500 mg. of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspension in aqueous and oily media or sterile solutions in a suitable solvent.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The therapeutic activity of the compounds of general formula I has been demonstrated by means of tests on standard laboratory animals. Such tests include, for example, the oral administration of the compounds to a strain of spontaneously hypertensive rats and the intraduodenal administration of the compounds to a strain of normotensive rats.

The compounds of general formula I in which n is 1 and $R_2$ is methyl may be prepared by reacting a β-ketosulphoxide of the general formula II

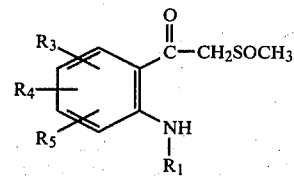

or the corresponding ylide of general formula III

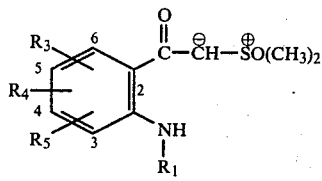

in which $R_1$, $R_3$, $R_4$ and $R_5$ are as hereinbefore defined with a tri(lower alkyl) orthoformate, especially trimethyl orthoformate or triethyl orthoformate.

The reaction involving the β-ketosulphoxide of formula II may be carried out in a conventional manner for such reactions, for example by heating a mixture of the β-ketosulphoxide, tri(lower alkyl) orthoformate and a base in a suitable solvent inert to the conditions of the reaction. As a suitable base an organic base, for example a secondary amine such as piperidine, may be used.

The reaction involving the ylide of formula III may be carried out in a conventional manner for such reactions, for example by heating a mixture of the ylide and a tri(lower alkyl) orthoformate and an acid in a suitable solvent inert to the conditions of the reaction. As a suitable acid an organic carboxylic acid, for example an aliphatic carboxylic acid such as acetic acid may be used. Preferred tri(lower alkyl) orthoformates for the reactions described above are trimethyl orthoformate and triethyl orthoformate.

The required β-ketosulphoxide or ylide for the above reactions may be prepared in a conventional manner from the appropriate N-$R_1$ substituted anthranilic acid. Reaction of this anthranilic acid with phosgene gives the 1,2-dihydro-1-$R_1$-2,4-dioxo-3,1-(4H)-benzoxazine of general formula IV

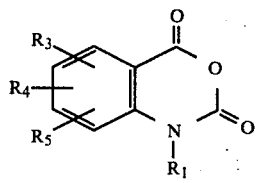

Reaction of the dihydrobenzoxazine IV with dimethylsulphoxide anion, sodium salt in a conventional manner gives the β-ketosulphoxide II. Reaction of the dihydrobenzoxazine IV with dimethylsulphoxonium methylide in a conventional manner gives the ylide III. The β-ketosulphoxide II may also be prepared by reacting an appropriately substituted anthranilic ester, for example the ethyl ester, with dimethylsulphoxide anion, sodium salt.

The compounds of general formula I may be prepared by cyclisation of an acrylate of the general formula V

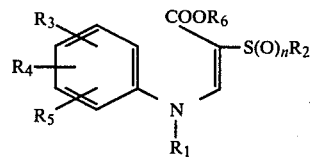

in which $R_1$, $R_2$, $R_3$, $R_4$, $R_5$ and n are as hereinbefore defined and $R_6$ is lower alkyl, preferably methyl or ethyl. The cyclisation may be effected in a conventional manner for similar reactions, for example by cyclisation in a mixture of acetic anhydride and concentrated sulphuric acid.

The acrylate of formula V may be prepared by reacting methyl $R_2$-thioacetate, methyl $R_2$-sulphinylacetate or methyl $R_2$-sulphonylacetate with sodium methoxide to give the corresponding anion, sodium salt which is then reacted with methyl formate to give the sodium salt of methyl 3-hydroxy-2-$R_2$-(thio or sulphinyl or sulphonyl) acrylate.

This compound is then reacted with the appropriately substituted N-$R_1$-aniline to give the acrylate V. These reactions may be carried out in a conventional manner for analagous reactions.

The acrylate of formula V in which n is 1 or 2 may also be prepared by oxidation of the corresponding acrylate in which n is 0. The reaction may be effected in a conventional manner, for example using an organic peracid as the oxidising agent.

The compounds of general formula I may be prepared by alkylation of the corresponding 1-unsubstituted quinolones of general formula VI

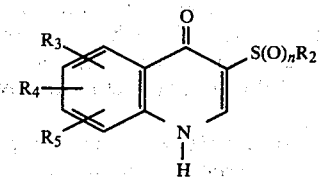

in which $R_2$, $R_3$, $R_4$, $R_5$ are as hereinbefore defined It will be appreciated by those skilled in the art that the 4-quinolones of formula VI are tautomeric with the corresponding 4-hydroxyquinoline compounds. However such compounds will hereinafter be referred to as 1-unsubstituted quinolines. The alkylation may be effected in a conventional manner for similar reactions using alkylating agents of formula $R_1$-X wherein X is chloro, bromo or iodo or of formula $(R_1)_2SO_4$, for example dimethyl sulphate.

The 1-unsubstituted quinolones of general formula VI in which n is 1 and $R_2$ is methyl may be prepared by reacting a β-ketosulphoxide of the above general formula II in which $R_1$ is hydrogen with a tri(lower alkyl) orthoformate, preferably trimethyl orthoformate. The reaction may be effected using piperidine or a mixture of ethanol and acetic acid as the reaction medium.

The 1-unsubstituted quinolones of the hereinbefore defined general formula VI provided that, when $R_3$, $R_4$ and $R_5$ are hydrogen, $R_2$ contains more than 1 carbon atom, are novel compounds and are valuable intermediates for the novel quinolones of general formula I.

The 1-unsubstituted quinolones of general formula VI may also be prepared by cyclisation of an acrylate of the above general formula V in which $R_1$ is hydrogen. The cyclisation may be carried out in a conventional manner for analogous reactions, for example by heating the acrylate in a suitable solvent inert to the conditions of the reaction, such as diphenyl ether.

Acrylates of the general formula V as hereinbefore defined, in which $R_1$ may also be hydrogen, are novel compounds and are valuable intermediates for the novel quinolones of general formula I.

The 1-unsubstituted quinolones of general formula VI in which n is 1 or 2 may be prepared by oxidation of the corresponding compounds in which n is 0 or 1. The oxidation may be effected in a conventional manner for analogous reactions, for example using an organic peracid as the oxidising agent.

The quinolones of general formula I in which n is 1 or 2 may also be prepared by oxidation of the corresponding compounds in which n is 0. The oxidation may be effected in a conventional manner for analogous oxidations of a sulphide, for example using an organic peracid as the oxidising agent. The sulphoxide (n=1) or sulphone (n=2) is formed, depending mainly on the amount of oxidising agent used. Similarly oxidation of the sulphoxide (n=1) gives the sulphone (n=2).

Thus 3-alkylthioquinolones of general formula I wherein n is 0 and $R_2$ is $C_{2-4}$ alkyl are valuable intermediates for the corresponding hereinbefore defined novel compounds of general formula I wherein n is 1 or 2. Subject to the hereinbefore defined provisos which designate the novel compounds of general formula I, such 3-alkylthioquinolones are novel compounds.

The quinolones of general formula I in which n is 0 may also be prepared by reduction of the corresponding compounds in which n is 1 using a conventional reducing agent, for example phosphorous trichloride.

The quinolones of general formula I in which one or more of $R_3$, $R_4$ and $R_5$ are alkoxy may also be prepared by alkylation of the corresponding hydroxy compounds using a conventional alkylating agent, for example an alkyl halide.

Ylides of general formula III as hereinbefore defined provided that at least one of $R_3$, $R_4$ and $R_5$ is other than hydrogen and, when $R_3$ and $R_4$ are hydrogen and $R_5$ is 4-methyl, $R_1$ is methyl are believed to be novel compounds. These ylides are valuable intermediates for the novel quinolones of general formula I in which n is 1 and $R_2$ is methyl.

It will be appreciated by those skilled in the art that, in the compounds of the hereinbefore defined general formula I in which n is 1, the group $R_2SO—$ contains a chiral centre at the sulphur atom. Thus such compounds exist in two diastereoisomeric forms. the present invention includes both diastereoisomers and the racemic mixture of them.

As mentioned above, the therapeutic activity of quinolones of general formula I has been demonstrated by tests which include (A) the oral administration of the compounds to a strain of spontaneously hypertensive rat and (B) the intraduodenal administration of the compounds to a strain or normotensive rat. These tests were carried out in the following way:

Test A

Female rats weight range 180–240 g., of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed around the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if it gave a reduction of blood pressure of 20% or greater at either of these time intervals.

Test B

Male normotensive rats (Wistar strain) of weight range 210–240 g. were used. The rats were anaesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose Blood pressure was recorded before dosing and for 30 minutes afterwards. Results were obtained as the mean of determinations in three rats per dosage level. Compounds which caused a fall in blood pressure of 10% or greater during the 30 minute post-dose period were designated as active.

The 1-substituted quinolone products of the following Examples 1–23 were found to be active in one or both of tests (A) and (B) at a dosage of 90 mg./kg. or less. In addition, the following known compounds were found to be active in one or both of the tests.

1-methyl-3-methylsulphinyl-4-quinolone
1-ethyl-3-methylsulphinyl-4-quinolone
1-methyl-3-methylthio-4-quinolone
1-methyl-3-methylsulphonyl-4-quinolone Particularly active novel quinolones of the present invention are those of the general formula VII

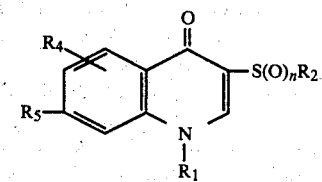

wherein
n is 0, 1 or 2; $R_1$ is $C_{1-4}$ alkyl, $R_2$ is $C_{1-4}$ alkyl and
(a) $R_5$ is hydrogen and $R_4$ is 6-lower alkoxy, 8-lower alkoxy, 5-halo or 6-halo;
(b) $R_4$ is hydrogen and $R_5$ is halo, lower alkyl, lower alkoxy, trifluoromethyl or lower alkylthio; or
(c) $R_5$ is halo, lower alkoxy or lower alkyl and $R_4$ is 6-lower alkyl, 6-lower alkoxy or 6-halo of a different value from $R_5$,
with the proviso that, when $R_4$ is hydrogen, $R_5$ is 7-methyl and $R_1$ is ethyl, $R_2$ contains more than one carbon atom.

Specific quinolones within the above general formula VII include the following compounds:

7-chloro-1-methyl-3-methylthio-4-quinolone
7-chloro-1-methyl-3-methylsulphinyl-4-quinolone
7-fluoro-1-methyl-3-methylthio-4-quinolone
7-fluoro-1-methyl-3-methylsulphinyl-4-quinolone
7-chloro-6-methoxy-1-methyl-3-methylsulphinyl-4-quinolone
7-fluoro-6-methoxy-1-methyl-3-methylsulphinyl-4-quinolone
7-fluoro-6-methoxy-1-methyl-3-methylthio-4-quinolone
7-tert-butyl-1-methyl-3-methylthio-4-quinolone
6,7-dimethoxy-1-methyl-3-methylsulphinyl-4-quinolone 7-tert-butyl-1-methyl-3-methylsulphinyl-4-quinolone
7-ethyl-1-methyl-3-methylsulphinyl-4-quinolone
1,7-dimethyl-3-methylsulphinyl-4-quinolone.

A preferred compound of the present invention is 7-fluoro-1-methyl-3-methylsulphinyl-4-quinolone.

The present invention provides a method of reducing blood pressure in a hypertensive warm blooded animal which comprises the administration of a quinolone compound of the hereinbefore defined general formula I. Administration may be arterial or parenteral; enteral administration, especially oral administration, is preferred. A suitable dosage for treating hypertension in warm blooded animals, including man, is generally within the range 0.1–100 mg./kg./day, more usually 0.5–75 mg./kg./day and especially 1–50 mg./kg./day, given in single or divided doses. Unit dosage forms suitably contain 1–500 mg., especially 5–500 mg., of the active compound.

The invention is illustrated by the following non-limitative Examples, in which parts and percentages are by weight and compositions of mixed solvents are given by volume. Novel compounds were characterised by one or more of the following spectroscopic techniques: nuclear magnetic resonance ($H^1$ or $C^{13}$), infra red and mass spectroscopy. Additionally, the products of the Examples had satisfactory elemental analyses. Melting points are given in degrees centigrade.

EXAMPLE 1

Trimethylsulphoxonium iodide (10.2 g.) was added gradually during 20 minutes at room temperature to a suspension of 50% sodium hydride (2.25 g.) in dry dimethyl sulphoxide (47 ml.). The mixture was stirred for a further 30 minutes at room temperature. A suspension of the known compound 1,2-dihydro-6,7-dimethoxy-1-methyl-2,4-dioxo-3,1-(4H)-benzoxazine (8.8 g.) in dry dimethyl sulphoxide (110 ml.) was added during 5 minutes, and the resulting solution was stirred at room temperature for 3 hours then at 50°–60° for a further 1 hour. The mixture was cooled and poured into ice-water (400 ml.) with stirring. The yellow-green precipitate was collected, washed with ether and dried in vacuo to give dimethyloxosulphonio-4,5-dimethoxy-2-methylaminobenzoylmethylide of m.p. 150°–153°, a novel compound.

A mixture of this ylide (5.4 g.), trimethyl orthoformate (40 ml.), absolute alcohol (40 ml.) and acetic acid (2.5 ml.) was heated under reflux with stirring for 3 hours. The mixture was distilled to one third of its original volume and cooled to room temperature. The resulting oil was washed with ether, dissolved in acetone and treated with petroleum (b.p. 60°–80°). The resulting solid was filtered off and dried in vacuo to give 6,7-dimethoxy-1-methyl-3-methylsulphinyl-4-quinolone m.p. 267°–268° (dec.).

EXAMPLE 2

In a similar manner to that described in Example 1, the known compound 1,2-dihydro-1,6-dimethyl-2,4-dioxo-3,1-(4H)-benzoxazine was converted to the novel ylide dimethyloxosulphonio-5-methylaminobenzoylmethylide m.p. 148°–150°, which was then reacted with trimethyl orthoformate to give 1,6-dimethyl-3-methylsulphinyl-4-quinolone, m.p. 202°–205°.

EXAMPLE 3

Anhydrous potassium carbonate (16.8 g.) was added gradually to a suspension of the known compound 1,2-dihydro-5-chloro-2,4-dioxo-3,1-(4H)-benzoxazine (11.7 g.) in dry dimethyl sulphoxide (110 ml.) and the mixture stirred at room temperature for 20 minutes Dimethyl sulphate (7 ml.) was added dropwise with vigorous stirring at 30°–35° for 12 minutes and the mixture allowed to settle. The supernatant liquid was decanted into an ice/dilute hydrochloric acid mixture (600 ml.; 0.05 M.HCl). The resulting precipitate was collected, washed with water and dried in vacuo to give 1,2-dihydro-1-methyl-5-chloro-2,4-dioxo-3,1-(4H)-benzoxazine m.p. 199°–201° (dec.).

In a similar manner to that described in Example 1, this benzoxazine was converted to the novel ylide dimethyloxosulphonio-6-chloro-2-methylaminobenzoylmethylide m.p. 72°–73° (dec.) which was then reacted with trimethyl orthoformate to give 5-chloro-1-methyl-3-methylsulphinyl-4-quinolone m.p. 208°–210° (dec.).

EXAMPLE 4

In a similar manner to that described in Example 1, the known compound, 1,2-dihydro-1-methyl-6-chloro-2,4-dioxo-3,1-(4H)-benzoxazine was converted to the novel ylide dimethyloxosulphonio-5-chloro-2-methylaminobenzoylmethylide m.p. 115°, which was then reacted with trimethyl orthoformate to give the 6-chloro-1-methyl-3-methylsulphinyl-4-quinolone m.p. 236°–238° (dec.).

EXAMPLE 5

Phosgene was bubbled through a solution of N-propylanthranilic acid (9.5 g.) in a mixture of concentrated hydrochloric acid (8 ml.) and water (80 ml.) at 50° for 2 hours.

The resulting precipitate was collected by filtration, washed with water and dried in vacuo to give 1,2-dihydro-1-propyl-2,4-dioxo-3,1-(4H)-benzoxazine m.p. 95°–96°, a novel compound.

In a similar manner to that described in Example 1 this benzoxazine was converted to the novel ylide dimethyloxosulphonio-2-propylaminobenzoylmethylide m.p. 132°–134°; which was then reacted with trimethyl orthoformate to give 3-methylsulphinyl-1-propyl-4-quinolone m.p. 126°–128° (from acetone:diethyl ether).

EXAMPLE 6

7-Fluoro-3-methylsulphinyl-4-quinolone (5.0 g.) was dissolved in hot butanone (250 ml.) containing anhydrous potassium carbonate (3.06 g.). The resulting suspension was stirred and treated dropwise with dimethyl sulphate (2.09 ml.). The mixture was stirred and boiled under reflux for 1 hour and filtered while hot. The filtrate was allowed to cool, giving a crystalline product. The product was collected and dried to give 7-fluoro-1-methyl-3-methylsulphinyl-4-quinolone, m.p. 226°–8°.

The intermediate 7-fluoro-3-methylsulphinyl-4-quinolone, was prepared in the following way.

A solution of 2-amino-4-fluorobenzoic acid (62 g.) in aqueous sodium carbonate (44 g. sodium carbonate in 1.6 liters water) was stirred and treated dropwise with a solution of phosgene (120 g.) in toluene (500 ml.) during 1.5 hours. The resulting suspension was stirred at room temperature for 24 hours. The solid product was collected by filtration, washed with water and dried to give 7-fluoro-1,2-dihydro-3,1-4H-benzoxazine-2,4-dione, m.p. 217°–219°.

A mixture of dimethyl sulphoxide (230 ml.), toluene (300 ml.) and 50% w/w dispersion of sodium hydride in mineral oil (20.7 g.) was heated under nitrogen at 65°–70° for 1 hour, then cooled to room temperature to form dimethylsulphoxide anion, sodium salt. The resulting suspension was stirred under nitrogen and the above benzoxazine-2,4-dione (27.5 g.) was added portionwise. The resulting solution was stirred at room temperature for 15 minutes and then poured into ether (3 liters). The resulting solid was collected by filtration and dissolved in water (300 ml.) and the solution acidified with glacial acetic acid to a final pH of 6.0. The solution was saturated with solid potassium carbonate. The resulting precipitate was collected, dried and recrystallised from ethanol/diethyl ether to give the novel compound 2'-amino-4'-fluoro-(2-methylsulphinyl)acetophenone, m.p. 115°–117° C.

This compound (14 g.) was dissolved in triethyl orthoformate (160 ml.) at 100° under nitrogen. The resulting solution was treated dripwise with piperidine (7 ml.). The mixture was heated with stirring at 120° C. under nitrogen for 30 minutes allowing ethanol produced to distil off, then cooled to room temperature. The solid product was collected, dried and crystalised from ethanol using charcoal to give the novel compound 7-fluoro-3-methylsulphinyl-4-quinolone, m.p. 265°.

EXAMPLE 7

In a similar manner to that described above 2'-amino-4'-chloro-(2-methylsulphinyl)acetophenone was reacted with triethyl orthoformate in the presence of piperidine to give the novel compound 7-chloro-3-methylsulphinyl-4-quinolone, m.p. 247°–249°. This product (65.8 g.) was dissolved in aqueous sodium hydroxide (14 g. sodium hydroxide in 250 ml. water). The solution was vigorously stirred and treated dropwise with dimethyl sulphate (30 ml.) during 20 minutes. The mixture was stirred at room temperature for a further period of 1 hour. The solid product was collected by filtration, washed with water, dried and crystallised from ethanol using charcoal to give 7-chloro-1-methyl-3-methylsulphinyl-4-quinolone, m.p. 245°–247°.

EXAMPLE 8

7-Bromo-3-methylsulphinyl-4-quinolone (1.07 g.) was dissolved in aqueous potassium hydroxide (0.3 g. potassium hydroxide in 30 ml. water). Dimethyl sulphate (0.4 ml.) was added and the mixture was stirred at room temperature for 3 hours. More dimethyl sulphate (0.5 ml.) was added and the mixture basified to pH 9.0 by the addition of aqueous KOH (0.4 N). The resulting mixture was stirred overnight. The solid product was collected by filtration and recrystallised from ethanol to give 7-bromo-1-methyl-3-methylsulphinyl-4-quinolone, m.p. 248°–249°.

The intermediate 7-bromo-3-methylsulphinyl-4-quinolone was prepared in the following way.

2-Amino-4-bromobenzoic acid was reacted with phosgene to give 7-bromo-1,2-dihydro-3,1-4H-benzoxazine-2,4-dione, m.p. 260°–262° (dec). This compound was converted to the novel compound 2'-amino-4'-bromo-(2-methylsulphinyl) acetophenone, m.p. 152°–154° (from ethanol). This compound was reacted with triethyl orthoformate in the presence of piperidine to give 7-bromo-3-methylsulphinyl-4-quinolone, m.p. 255°–256° (from ethanol). These reactions were carried out in a similar way to those described in Example 1.

EXAMPLE 9

A solution of 7-chloro-1-methyl-3-methylsulphinyl-4-quinolone (1.25 g.) in chloroform (20 ml.) was added dropwise to a solution of phosphorus trichloride (1.3 ml.) in chloroform (10 ml.) at 0°–5°. The mixture was stirred at room temperature for 2 hours and then left at room temperature overnight. The solid product was filtered off, washed with chloroform, and dried. The product was stirred with saturated aqueous sodium bicarbonate (100 ml.) for 30 minutes, then collected by filtration, washed with water and dried. Recrystallisation from ethanol gave 7-chloro-1-methyl-3-methylthio-4-quinolone, m.p. 173°–175°.

EXAMPLE 10

A solution of 3-chloroperoxybenzoic acid (85%, 6.75 g.) in chloroform (70 ml.) was added dropwise to a stirred solution of 7-chloro-1-methyl-3-methylsulphinyl-4-quinolone (6.25 g.) in chloroform (150 ml.). The resulting solution was stirred at room temperature for 2 hours and then washed repeatedly with saturated aqueous sodium carbonate solution to remove peroxide. The resulting solution was dried over anhydrous magnesium sulphate and then evaporated. The solid residue was crystallised from ethanol using charcoal to give 7-chloro-1-methyl-3-methylsulphonyl-4-quinolone, m.p. 241°–242°.

EXAMPLE 11

Dimethyl sulphate (2.2 ml.) was added dropwise to a stirred mixture of 7-chloro-6-methoxy-3-methylthio-4-quinolone (5.42 g., containing some 5-chloro isomer), anhydrous potassium carbonate (3.2 g.) and butanone (400 ml.). The mixture was boiled under reflux overnight and filtered while hot. The hot filtrate was cooled to cause crystallisation of the product 7-chloro-6-methoxy-1-methyl-3-methylthio-4-quinolone, m.p. 220°–222°.

The starting material for the above reaction was prepared as follows:

Sodium (7.65 g.) was dissolved in anhydrous methanol (450 ml.) and the solution evaporated to dryness. The resulting sodium methoxide was suspended in anhydrous diethyl ether (300 ml.). The suspension was stirred at 0° and methyl methylthioacetate (40 g.) was added dropwise. The mixture was stirred at 0° for 1 hour and then treated dropwise with methyl formate (21 g.). The mixture was stirred at 0° for 1 hour and then stirred overnight at room temperature. The resulting suspension of solid was extracted with water (300 ml.) and the aqueous extract adjusted to 333 ml. with water. This aqueous extract containing methyl-3-hydroxy-2-methylthioacrylate, sodium salt (0.33 mole) was added to a stirred solution of 3-chloro-4-methoxyaniline (52 g.) in a mixture of water (800 ml.) and 11.6 N hydrochloric acid (33 ml.) at 0°. The mixture was stirred for 30 minutes and the product collected by filtration to give the novel intermediate compound methyl 3-(3-chloro-4-methoxyanilino)-2-methylthioacrylate, m.p. 110°–112°. This acrylate (77.6 g.) was added to diphenyl ether (200 ml.) stirred at 250° under nitrogen. After stirring at 250° for 15 minutes the mixture was cooled. The resulting precipitate was collected by filtration to give the novel intermediate compound 7-chloro-6-methoxy-3-methylthio-4-quinolone, m.p. 288°–290° (dec.) Examination by thin layer chromatography showed the presence of a minor amount of the corresponding 5-chloro isomer.

EXAMPLE 12

7-Chloro-6-methoxy-1-methyl-3-methylthio-4-quinolone (1.5 g). was dissolved in dichloromethane (75 ml.) and the resulting solution treated dropwise at −20° with a solution of 3-chloroperbenzoic acid (85%, 1.003 g.) in dichloromethane (75 ml.). The reaction mixture was poured into saturated aqueous sodium bicarbonate (300 ml.) and the mixture extracted with dichloromethane (4×50 ml.). The peroxide-free organic extract was dried and evaporated. The resulting solid was recrystallised from ethyl acetate:methanol to give 7-chloro-6-methoxy-1-methyl-3-methylsulphinyl-4-quinolone, m.p. 263°–265°.

EXAMPLE 13

In a similar way to that described in Example 11, the appropriate 1-unsubstituted quinolones were methylated to give the following compounds (a)–(e). Compounds (f)–(n) were prepared in a similar manner except that for compounds (f)–(j) the methylation was carried out in aqueous potassium hydroxide at 0°–5°, and in aqueous sodium hydroxide at room temperature for compounds (k)–(n).

(a) 1-methyl-3-methylthio-7-trifluoromethyl-4-quinolone, m.p. 160°–162°.
(b) 7-t-butyl-1-methyl-3-methylthio-4-quinolone, m.p. 165°–168° (from ethyl acetate)
(c) 7-chloro-1,6-dimethyl-3-methylthio-4-quinolone, m.p. 211°–212° (from ethanol)
(d) 1,5,7-trimethyl-3-methylthio-4-quinolone, m.p. 146°–147° (from ethanol)
(e) 5,7-dichloro-1-methyl-3-methylthio-4-quinolone, m.p. 194°–195°
(f) 7-methoxy-1-methyl-3-methylthio-4-quinolone, m.p. 155°–157° (from ethyl acetate:light petroleum)
8-fluoro-1-methyl-3-methylthio-4-quinolone, m.p. 145°–147°
(h) 7-chloro-3-ethylthio-1-methyl-4-quinolone, m.p. 146°–148° (from ethanol)
(i) 6-acetyl-1-methyl-3-methylthio-4-quinolone, m.p. 183°–184° (from ethyl acetate:light petroleum)
(j) an isomeric mixture of 7-acetyl-1-methyl-3-methylthio-4-quinolone and 5-acetyl-1-methyl-3-methylthio-4-quinolone, m.p. 148°–150°.
(k) 6-chloro-7-methoxy-1-methyl-3-methylthio-4-quinolone, m.p. 227°–229° (from butanone)
(l) 7-fluoro-6-methoxy-1-methyl-3-methylthio-4-quinolone, m.p. 210°–212° (from ethanol)
(m) 1-methyl-3-methylthio-7-isopropyl-4-quinolone, m.p. 114°–115° (from ethanol:diethyl ether)
(n) an isomeric mixture of 7-fluoro- and 5-fluoro-1-methyl-3-methylthio-4-quinolone. Isomers separated by high pressure liquid chromatography over silica gel. Elution with ethyl acetate at a flow rate of 200 ml. per minute gave 7-fluoro-1-methyl-3-methylthio-4-quinolone, m.p. 261°–263°.

The required 1-H-4-quinolones for the above reactions were prepared in a similar way to that described in Example 11. The appropriate aniline was converted to the acrylate ester of formula VIII which was then cyclised to give the quinolone of formula IX

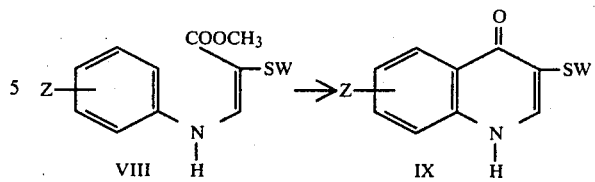

In this way the following novel intermediates were prepared

| Z | W | m.p.° |
|---|---|---|
| Acrylates of formula VIII | | |
| 3-CF$_3$ | CH$_3$ | 73–75 |
| 3-t-butyl | CH$_3$ | 53–54 |
| 3-Cl—4-CH$_3$ | CH$_3$ | 88–90 |
| 3,5-(CH$_3$)$_2$ | CH$_3$ | 94–96 |
| 3,5-Cl$_2$ | CH$_3$ | 124–128 |
| 3-OCH$_3$ | CH$_3$ | 76–78 |
| 2-F | CH$_3$ | oil |
| 3-Cl | C$_2$H$_5$ | 56–58 |
| 4-OCOCH$_3$ | CH$_3$ | 85–87 |
| 3-OCOCH$_3$ | CH$_3$ | 73–75 |
| 3-OCH$_3$—4-Cl | CH$_3$ | 115–116 |
| 3-F—4-OCH$_3$ | CH$_3$ | 85–86 |
| 3-isopropyl | CH$_3$ | 50–52 |
| 3-F | CH$_3$ | 83–86 |
| Quinolones of formula IX | | |
| 7-CF$_3$* | CH$_3$ | 300–305 |
| 7-t-butyl | CH$_3$ | 239–240 |
| 7-Cl—6-CH$_3$ | CH$_3$ | 310 |
| 5,7-(CH$_3$)$_2$ | CH$_3$ | 238–240 |
| 5,7-Cl$_2$ | CH$_3$ | 314–316 |
| 7-OCH$_3$* | CH$_3$ | 218–220 |
| 8-F | CH$_3$ | 213–215 |
| 7-Cl | C$_2$H$_5$ | 248–250 |
| 6-COCH$_3$ | CH$_3$ | 265–269 |
| 7-COCH$_3$* | CH$_3$ | 189–191 |
| 6-Cl—7-OCH$_3$* | CH$_3$ | 315–320 (dec) |
| 6-OCH$_3$—7-F* | CH$_3$ | 292–294 |
| 7-isopropyl | CH$_3$ | 149–151 |
| 7-F* | CH$_3$ | 234–236 |

*Corresponding 5-isomer also present. Product used for next stage without any separation of isomers.

EXAMPLE 14

In a similar manner to that described in Example 12, the sulphides (a)–(k) of Example 13 were oxidised to the following sulphoxides:

(a) 1-methyl-3-methylsulphinyl-7-trifluoromethyl-4-quinolone, m.p. 218°–220° (from cyclohexane:ethyl acetate).
(b) 7-t-butyl-1-methyl-3-methylsulphinyl-4-quinolone, m.p. 209°–210° (from butanone)
(c) 7-chloro-1,6-dimethyl-3-methylsulphinyl-4-quinolone, m.p. 257°–258° (from ethanol)
(d) 1,5,7-trimethyl-3-methylsulphinyl-4-quinolone, m.p. 248°–250° (from ethanol)
(e) 5,7-dichloro-1-methyl-3-methylsulphinyl-4-quinolone, m.p. 241°–242° (from ethanol)
(f) 7-methoxy-1-methyl-3-methylsulphinyl-4-quinolone, m.p. 233°–235° (from ethyl acetate:light petroleum)
(g) 8-fluoro-1-methyl-3-methylsulphinyl-4-quinolone, m.p. 161°–162° (from ethyl acetate:light petroleum)
(h) 7-chloro-3-ethylsulphinyl-1-methyl-4-quinolone, m.p. 180°–182° (from ethyl acetate:ethanol)
(i) 6-acetyl-1-methyl-3-methylsulphinyl-4-quinolone, m.p. 254°–255° (from ethyl acetate:methanol)

(j) 7-acetyl-1-methyl-3-methylsulphinyl-4-quinolone, m.p. 245°–246°.

This compound was isolated by evaporating the organic extract to give a solid which was purified (including removal of 5-acetyl isomer) by high pressure liquid chromotography. A column 5.7 cm.×30 cm. containing 420 g. silica gel coated with 11% octadecylsilane was used. The product was eluted in the reverse phase mode with methanol:water 35:65 at 100 ml. per minute.

(k) 6-chloro-7-methoxy-1-methyl-3-methylsulphinyl-4-quinolone, m.p. 278°–279° (from ethanol)

EXAMPLE 15

In a similar way to that described in Example 11, an aqueous solution of 3-hydroxy-2-methylthioacrylate was prepared using 17.5 g. sodium, 91.2 g. methyl methylthioacetate and 54.9 g. methyl formate. This product was then reacted with N-methyl-3-ethylaniline (101 g.) in a similar way to that described in Example 11 and the product isolated by extraction with ethyl acetate to give methyl 2-(3-ethyl-N-methylanilino)-1-methylthioacrylate as an oil. Concentrated sulphuric acid (10 ml.) was added dropwise to a stirred solution of this acrylate (10 g.) in acetic anhydride (20 ml.) at room temperature, causing the mixture to boil. The mixture was cooled to room temperature, poured on to ice/water (300 ml.) and extracted with ethyl acetate (3×200 ml.) and then dichloromethane (2×150 ml.). The combined extracts were dried and evaporated to give a mixture of the isomers 5-ethyl-1-methyl-3-methylthio-4-quinolone and 7-ethyl-1-methyl-3-methylthio-4-quinolone, isolated as an oily solid. The isomers are separated by high pressure liquid chromatography using a cartridge 5.7 cm.×30 cm. containing 325 g. silica gel.

Elution with dichloromethane:isopropanol 96:4 at a flow rate of 200 ml. per minute gave the isomers:

(a) 5-ethyl-1-methyl-3-methylthio-4-quinolone m.p. 148°–150°, and (b) 7-ethyl-1-methyl-3-methylthio-4-quinolone, m.p. 138°–140°

Products (a) and (b) were crystallised from toluene and characterised by NMR.

The following compounds were prepared in a similar manner without using high pressure liquid chromatography (c) 1-methyl-3-propylthio-4-quinolone, m.p. 74°–76° (from ethyl acetate:light petroleum)

(d) 3-ethylthio-1-methyl-4-quinolone, m.p. 115°–117° (from ethanol:diethyl ether)

(e) 3-n-butylthio-1-methyl-4-quinolone, m.p. 53°–55° (from ethyl acetate:light petroleum).

(f) 8-methoxy-1-methyl-3-methylthio-4-quinolone, m.p. 133°–135° (from ethyl acetate:light petroleum)

(g) A mixture of the isomers 1,6,7-trimethyl-3-methylthio-4-quinolone and 1,5,6-trimethyl-3-methylthio-4-quinolone m.p. 132°–134°

The intermediate acrylates for the above quinolones (c)–(g) were isolated as oils which were cyclised to the quinolones without purification.

EXAMPLE 16

In a similar manner to that described in Example 12, the sulphides (a)–(g) of Example 15 were oxidised to the following sulphoxides:

(a) 5-ethyl-1-methyl-3-methylsulphinyl-4-quinolone, m.p. 196°–197°. Product purified by crystallisation from ethanol followed by high pressure liquid chromatography over silica gel and elution with methylene chloride:isopropanol (9:1) at a flow rate of 200 ml. per minute.

(b) 7-ethyl-1-methyl-3-methylsulphinyl-4-quinolone, m.p. 227°–229°

(c) 1-methyl-3-propylsulphinyl-4-quinolone, m.p. 153°–155°. Purified by preparative layer chromatography on silica gel using dichloromethane:ethanol 95:5 as eluant and extracting the produce with ethanol (d) 3-ethylsulphinyl-1-methyl-4-quinolone, m.p. 160°–163° Purified as described above for (c)

(e) 3-n-butylsulphinyl-1-methyl-4-quinolone, m.p. 105°–106° Purified as described above for (c) after crystallisation from ethyl acetate:light petroleum and then toluene:diethyl ether (f) 8-methoxy-1-methyl-3-methylsulphinyl-4-quinolone, m.p. 147°–148° (from ethyl acetate:light petroleum)

Product from oxidation of Example 15 (g) isolated by extraction with dichloromethane. Product purified by high pressure liquid chromatography over silica gel. Elution with ethyl acetate:methylene chloride:ethanol (45:45:10) at 200 ml. per minute gave:

(g) 1,5,6-trimethyl-3-methylsulphinyl-4-quinolone, m.p. 250–252 (from ethanol), and (h) 1,6,7-trimethyl-3-methylsulphinyl-4-quinolone, m.p. 253°–254° (from ethanol).

EXAMPLE 17

In a similar way to that described in Example 6, the appropriate 1-unsubstituted quinolones were methylated to give the following compounds (a)–(f)

(a) 6-methoxy-1-methyl-3-methylsulphinyl-4-quinolone m.p. 189°–190°

(b) 6-fluoro-1-methyl-3-methylsulphinyl-4-quinolone, m.p. 239°–241° (from ethanol)

(c) 6,7,8-trimethoxy-1-methyl-3-methylsulphinyl-4-quinolone m.p. 178°–179°

(d) 1,8-dimethyl-3-methylsulphinyl-4-quinolone, m.p. 199°–200°

(e) 8-chloro-1-methyl-3-methylsulphinyl-4-quinolone, m.p. 170°–171°

(f) 1,7-dimethyl-3-methylsulphinyl-4-quinolone, m.p. 224°–226° (from ethanol).

The required 1-H-4-quinolones for the above reactions were prepared in a similar way to that described in Example 6. The appropriate anthranilic acid was converted to the benzoxazine X which was then converted to the β-ketosulphoxide XI which then underwent ring closure to give the 1-H-quinolone XII

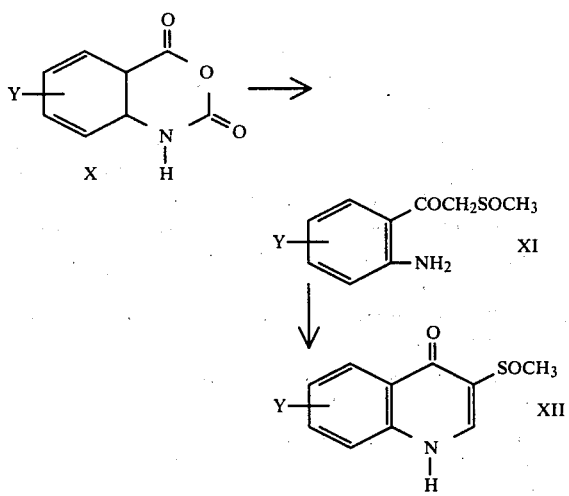

In this way the following novel intermediates were prepared. When required, crystallisation was effected with ethanol or ethyl acetate.

| Benzoxazines and β-ketosulphoxides | | |
|---|---|---|
| Y | X m.p.° | XI m.p.° |
| 6-OCH$_3$ | 234–236 | 125–126 |
| 6-F | 256–258* | 95–97 |
| 6,7,8-(OCH$_3$)$_3$ | 250–252 | 97–98 |
| 8-CH$_3$ | 278–280 | 148–149 |
| 8-Cl | 229–232 | 132–133 |
| 7-CH$_3$ | * | 104–105 |

*known compound

| Quinolones of formula XII | |
|---|---|
| Y | m.p.° of compound |
| 6-OCH$_3$ | 255–257 |
| 6-F | 214–215 |
| 6,7,8-(OCH$_3$)$_3$ | 171–173 |
| 8-CH$_3$ | 249–250 |
| 8-Cl | 238–240 |
| 7-CH$_3$ | 238–240 |

EXAMPLE 18

A mixture of 3-methylsulphinyl-4-quinolone (1.035 g.), anhydrous potassium carbonate (1.38 g.), n-butyl bromide (0.685 g.) and dry acetone (50 ml.) was refluxed for 24 hours. The mixture was filtered and the filtrate evaporated to dryness. The resulting oil was dissolved in chloroform (50 ml.). The solution was washed with water, dried and evaporated. The residue oil was triturated with light petroleum to give the solid product 1-n-butyl-3-methylsulphinyl-4-quinolone, m.p. 103°–105°.

In similar manner 3-methylsulphinyl-4-quinolone was alkylated with the following alkylating agents R$_{10}$-V where V=Br or Cl to give the products 1-R$_{10}$-3-methylsulphinyl-4-quinolone with melting points given below:

| R$_{10}$ | V | m.p.° of product |
|---|---|---|
| n-pentyl | Br | 83–85 |
| n-hexyl | Br | 77–78* |
| benzyl | Br | 210–212* |
| allyl | Br | 144–146 |
| propargyl | Br | 245 (dec.) |
| CH$_2$COOC$_2$H$_5$ | Cl | 229–230 |
| CH$_2$CH$_2$OH | Br | 190–191 |

-continued

| R$_{10}$ | V | m.p.° of product |
|---|---|---|
| 3,4-dimethoxy-benzyl | Cl | 151–152** |

*recrystallised from light petroleum
**recrystallised from ethyl acetate

EXAMPLE 19

Using the method described in Example 12, the following oxidations were carried out with 3-chloroperbenzoic acid as the oxidising agent.

(a) 7-methoxy-1-methyl-3-methylthio-4-quinolone was oxidised in chloroform at 0°–5° to give 7-methoxy-1-methyl-3-methylsulphonyl-4-quinolone, m.p. 212°–214° (from ethyl acetate:methanol).

(b) 7-fluoro-1-methyl-3-methylthio-4-quinolone was oxidised in dichloromethane at 20° to give 7-fluoro-1-methyl-3-methylsulphonyl-4-quinolone, m.p. 231°–236° (from ethanol)

(c) 1-methyl-3-methylsulphinyl-7-trifluoromethyl-4-quinolone was oxidised in dichloromethane at 0° to give 1-methyl-3-methylsulphonyl-7-trifluoromethyl-4-quinolone, m.p. 300°–301° (from methanol:ethyl acetate)

(d) 3-n-butylthio-1-methyl-4-quinolone was oxidised in chloroform at 0° to give 3-n-butylsulphonyl-1-methyl-4-quinolone, m.p. 107°–107.5° (from ethyl acetate:ethanol)

(e) 3-ethylthio-1-methyl-4-quinolone was oxidised in dichloromethane at 20° to give 3-ethylsulphonyl-1-methyl-4-quinolone, m.p. 164°–166°.

(f) 7-t-butyl-1-methyl-3-methylsulphinyl-4-quinolone was oxidised in chloroform at 20° to give 7-t-butyl-1-methyl-3-methylsulphonyl-4-quinolone, m.p. 247°–248° (from ethanol).

EXAMPLE 20

A mixture of 7-methoxy-1-methyl-3-methylthio-4-quinolone (8.23 g.) glacial acetic acid (75 ml.) and hydrobromic acid (75 ml.) was stirred and boiled under reflux for 2 days. The mixture was cooled and poured into saturated aqueous sodium bicarbonate (500 ml.). The resulting precipitate was collected by filtration and dried to give 7-hydroxy-1-methyl-3-methylthio-4-quinolone, m.p. 285°–288°.

A mixture of this compound (1.65 g.), potassium carbonate (3.105 g.), 1-iodobutane (1.5 g.) and dry acetone (150 ml.) was refluxed overnight. The hot reaction mixture was filtered. The filtrate was evaporated to give a sticky solid which was triturated with diethyl ether to give 7-n-butoxy-1-methyl-3-methylthio-4-quinolone, m.p. 88°–92°

A portion of this sulphide was oxidised with 3-chloroperbenzoic acid in chloroform at −20° in an analogous manner to that described in Example 12 to give 7-n-butoxy-1-methyl-3-methylsulphinyl-4-quinolone, m.p. 148°–150° (from ethyl acetate:light petroleum).

EXAMPLE 21

(a) In a similar manner to that described in Example 12, the compound 7-fluoro-6-methoxy-1-methyl-3-methylthio-4-quinolone of Example 13 was oxidised to give 7-fluoro-6-methoxy-1-methyl-3-methylsulphinyl-4-quinolone, m.p. 263°–264° (from ethanol).

(b) Similarly, the compound 1-methyl-3-methylthio-7-isopropyl-4-quinolone of Example 13 was oxidised to give the compound 1-methyl-3-methylsulphinyl-7-isopropyl-4-quinolone, m.p. 214°–215° (from ethanol).

EXAMPLE 22

Using the methods described in Example 11 and Example 12, 3-methylthioaniline was converted to methyl 3-(3-methylthioanilino)-2-methylthioacrylate, m.p. 90°–92°. This acrylate was cyclised to give 3,7-bis(methylthio)4-quinolone, m.p. 197°–200°, containing the corresponding 5-methylthio isomer. This product was methylated with dimethyl sulphate in aqueous potassium hydroxide at room temperature to give a mixture of 1-methyl-3,7-bis (methylthio)-4-quinolone and 1-methyl-3,5-bis(methylthio)-4-quinolone. This mixture was separated by high pressure liquid chromatography to give 1-methyl-3,7-bis(methylthio)-4-quinolone, m.p. 154°–155° (from ethanol). Oxidation of this compound with 3-chloroper benzoic acid gave 1-methyl-3-methylsulphinyl-7-methylthio-4-quinolone, m.p. 196°–198° (from ethanol).

EXAMPLE 23

In a similar way to that described in Example 22, the following compounds were prepared: 3-(3-chloro-4-fluoroanilino)-2-methylthioacrylate, m.p. 80°–82°. Cyclisation gave an isomeric mixture of 7-(and 5-)chloro-6-fluoro-3-methylthio-4-quinolone, m.p. 250°–252°. This product was methylated to give an isomeric mixture of 7-(and 5-)chloro-6-fluoro-1-methyl-3-methylthio-4-quinolone, m.p. 90°–93°. Oxidation of this product with 3-chloroperbenzoic acid gave an isomeric mixture of 7-(and 5)chloro-6-fluoro-1-methyl-3-methylsulphinyl-4-quinolone, m.p. 236°–237°.

EXAMPLE 24

In the preparation of tablets, the following mixture is dry granulated and compressed in a tabletting machine to give tablets containing 10 mg. of active ingredient:

| | |
|---|---|
| 6,7-Dimethoxy-1-methyl-3-methylsulphinyl-4-quinolone | 10g. |
| Lactose | 5g. |
| Calcium phosphate | 5g. |
| Maize Starch | 5g. |

In a similar manner tablets are prepared containing 25 mg. of active ingredient.

EXAMPLE 25

In a similar manner to that described in Example 24, there are prepared tablets containing 10 mg. or 25 mg. of 1-methyl-3-methylsulphinyl-4-quinolone as the active ingredient.

EXAMPLE 26

In the preparation of enteric coated tablets, the tablets described in Examples 24 and 25 are given a thin coat of shellac varnish, followed by 20 coats of cellulose acetate phthalate.

EXAMPLE 27

In the preparation of capsules, a mixture of equal parts by weight of 6,7-dimethoxy-1-methyl-3-methylsulphinyl-4-quinolone and calcium phosphate is encapsulated in hard gelatin capsules, each capsule containing 10 mg. of active ingredient.

Capsules containing 25 mg. of active ingredient are prepared in a similar manner.

EXAMPLE 28

In a similar manner to that described in Example 27, there are prepared capsules containing 10 mg. or 25 mg. of 1-methyl-3-methylsulphinyl-4-quinolone as the active ingredient.

EXAMPLE 29

In the preparation of enteric coated capsules, the capsules of Examples 27 and 28 are coated with cellulose acetate phthalate in a conventional manner.

EXAMPLE 30

In the manner described in Example 24, there are prepared tablets containing 10 mg. or 25 mg. of one of the following active ingredients:

7-fluoro-1-methyl-3-methylsulphinyl-4-quinolone
7-chloro-6-methoxy-1-methyl-3-methylsulphinyl-4-quinolone
7-tert-butyl-1-methyl-3-methylsulphinyl-4-quinolone.

EXAMPLE 31

In the manner described in Example 27, there are prepared capsules containing 10 mg. or 25 mg. of the active ingredients listed in Example 30.

EXAMPLE 32

Suppositories weighing 1 g. and containing 25 mg. active ingredient are prepared in a conventional manner using a base consisting of:

| | |
|---|---|
| polyethylene glycol 4000 | 33% |
| polyethylene glycol 6000 | 47% |
| water | 20% |

Suitable active ingredients include those listed in Examples 24, 25 and 30.

We claim:

1. Quinolone compounds of the general formula

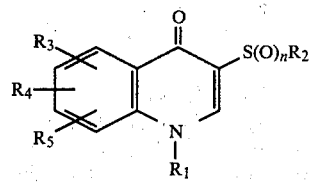

wherein n is 0, 1 or 2; $R_1$ is lower alkyl optionally substituted by hydroxy or $C_{1-4}$ alkoxycarbonyl; allyl; propynyl or phenyl-lower alkyl in which the phenyl ring is optionally substituted by 1 or 2 $C_{1-4}$ alkoxy groups; $R_2$ is $C_{1-4}$ alkyl; and $R_3$ $R_4$ and $R_5$, which may be the same or different, are hydrogen, lower alkyl, lower alkoxy, lower alkanoyl, halo, trifluoromethyl or lower alkylthio, with the provisos that
   (a) when $R_3$, $R_4$ and $R_5$ are hydrogen $R_2$ is methyl and $R_1$ is lower alkyl, $R_1$ contains more than one carbon atom, and
   (b) when $R_3$ and $R_4$ are hydrogen, $R_5$ is hydrogen or 7-methyl, and $R_1$ is ethyl, $R_2$ contains more than one carbon atom.

2. Quinolone compounds of the general formula

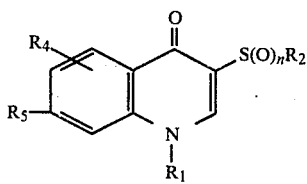

wherein n is 0, 1 or 2; $R_1$ is $C_{1-4}$ alkyl, $R_2$ is $C_{1-4}$ alkyl and
(a) $R_5$ is hydrogen and $R_4$ is 6-lower alkoxy, 8-lower alkoxy, 5-halo or 6-halo;
(b) $R_4$ is hydrogen and $R_5$ is halo, lower alkyl, lower alkoxy, trifluoromethyl or lower alkylthio; or
(c) $R_5$ is halo, lower alkoxy or lower alkyl and $R_4$ is 6-lower alkyl, 6-lower alkoxy or 6-halo of a different value from $R_5$, with the proviso that, when $R_4$ is hydrogen, $R_5$ is 7-methyl and $R_1$ is ethyl, $R_2$ contains more than one carbon atom.

3. A compound as claimed in claim 2 wherein $R_1$ and $R_2$ are methyl.

4. A compound as claimed in claim 2 wherein $R_4$ is hydrogen and $R_5$ is halo, lower alkyl or trifluoromethyl.

5. A compound as claimed in claim 4 wherein $R_5$ is halo.

6. A compound as claimed in claim 2 wherein $R_4$ is 6-lower alkoxy and $R_5$ is halo or lower alkoxy.

7. A compound as claimed in claim 2 wherein $R_4$ is 6-halo and $R_5$ is lower alkyl.

8. A compound as claimed in claim 4 wherein $R_5$ is $C_1$-$C_4$ alkyl.

9. 7-Fluoro-1-methyl-3-methylsulphinyl-4-quinolone.

10. Therapeutic compositions suitable for antihypertensive use which comprise as an active ingredient an antihypertensive amount of a quinolone compound of the general formula

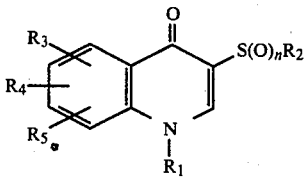

wherein n is 0, 1 or 2; $R_1$ is lower alkyl optionally substituted by hydroxy or $C_{1-4}$ alkoxycarbonyl; allyl; propynyl or phenyl-lower alkyl in which the phenyl ring is optionally substituted by 1 or 2 $C_{1-4}$ alkoxy groups; $R_2$ is $C_{1-4}$ alkyl with the proviso that when n is 0, $R_2$ is methyl; and $R_3$, $R_4$ and $R_5$, which may be the same or different, are hydrogen, lower alkyl, lower alkoxy, lower alkanoyl, halo, trifluoromethyl or lower alkylthio, together with a pharmaceutically acceptable carrier.

11. Therapeutic compositions as claimed in claim 10 in unit dosage form.

12. Therapeutic compositions as claimed in claim 11 wherein the unit dosage of active ingredient is 1–500 mg.

13. Therapeutic compositions as claimed in claim 12 in the form of tablets, capsules or suppositories.

14. A therapeutic composition as claimed in any of claims 10 through 13, wherein the quinoline compound has the formula

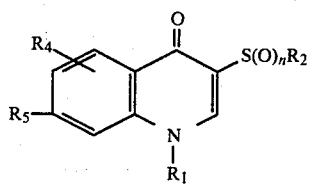

wherein n is 0, 1 or 2; $R_1$ is $C_{1-4}$ alkyl, $R_2$ is $C_{1-4}$ alkyl and
(a) $R_5$ is hydrogen and $R_4$ is 6-lower alkoxy, 8-lower alkoxy, 5-halo or 6-halo;
(b) $R_4$ is hydrogen and $R_5$ is halo, lower alkyl, lower alkoxy, trifluoromethyl or lower alkylthio; or
(c) $R_5$ is halo, lower alkoxy or lower alkyl and $R_4$ is 6-lower alkyl, 6-lower alkoxy or 6-halo of a different value from $R_5$.

15. Therapeutic compositions as claimed in any one of claims 10–13 wherein the quinolone compound is 7-fluoro-1-methyl-3-methylsulphinyl-4-quinolone.

16. Therapeutic compositions as claimed in any one of claims 10–13 wherein the quinolone compound is 1-methyl-3-methylsulphinyl-4-quinolone.

17. Quinolone compounds of the general formula

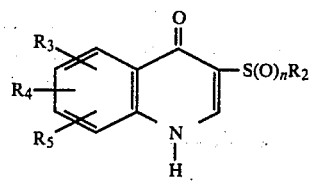

wherein n is 0, 1 or 2, $R_2$ is $C_{1-4}$ alkyl and $R_3$, $R_4$ and $R_5$ which may be the same or different, are hydrogen, lower alkyl, lower alkoxy, lower alkanoyl, halo, trifluoromethyl or lower alkylthio, with the proviso that, when $R_3$, $R_4$ and $R_5$ are hydrogen, $R_2$ contains more than 1 carbon atom.

18. Therapeutic compositions as claimed in any one of claims 10 through 13 wherein the quinolone compound is as defined in claim 3.

19. Therapeutic compositions as claimed in any one of claims 10 through 13 wherein the quinolone compound is as defined in claim 4.

20. Therapeutic compositions as claimed in any one of claims 10 through 13 wherein the quinolone compound is as defined in claim 5.

21. Therapeutic compositions as claimed in any one of claims 10 through 13 wherein the quinolone compound is as defined in claim 6.

22. Therapeutic compositions as claimed in any one of claims 10 through 13 wherein the quinolone compound is as defined in claim 7.

23. Therapeutic compositions as claimed in any one of claims 10 through 13 wherein the quinolone compound is as defined in claim 8.

24. A method of treating hypertension in a hypertensive warm blooded animal which comprises administering to the hypertensive animal a therapeutically effective amount of a quinolone compound of the formula

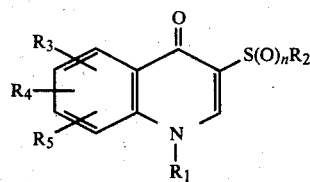

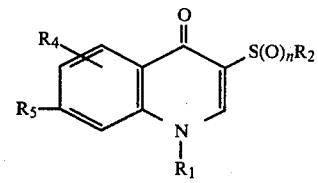

wherein n is 0, 1, or 2; $R_1$ is lower alkyl optionally substituted by hydroxy or $C_{1-4}$ alkoxycarbonyl; allyl; propynyl or phenyl-lower alkyl in which the phenyl ring is optionally substituted by 1 or 2 $C_{1-4}$ alkoxy groups; $R_2$ is $C_{1-4}$ alkyl with the proviso that when n is 0, $R_2$ is methyl; and $R_3$, $R_4$, and $R_5$, which may be the same or different, are hydrogen, lower alkyl, lower alkoxy, lower alkanoyl, halo, trifluoromethyl, or lower alkylthio.

25. The method of claim 24, wherein the compound is administered together with a pharmaceutically-acceptable carrier.

26. The method of claim 24, wherein the compound is administered in unit dosage form.

27. The method of claim 26, wherein the amount of the compound in the unit dosage form is 1–500 mg.

28. The method of claim 24, wherein the compound is administered in the form of a tablet, capsule, or suppository.

29. The method of claim 24, wherein the compound is 7-fluoro-1-methyl-3-methylsulphinyl-4-quinoline.

30. The method of claim 24, wherein the compound is 1-methyl-3-methylsulphinyl-4-quinolone.

31. A method as claimed in claim 24, wherein the quinolone compound has the formula wherein n is 0, 1 or 2; $R_1$ is $C_{1-4}$ alkyl, $R_2$ is $C_{1-4}$ alkyl and
  (a) $R_5$ is hydrogen and $R_4$ is 6-lower alkoxy, 8-lower alkoxy, 5-halo or 6-halo;
  (b) $R_4$ is hydrogen and $R_5$ is halo, lower alkyl, lower alkoxy, trifluoromethyl or lower alkylthio; or
  (c) $R_5$ is halo, lower alkoxy or lower alkyl and $R_4$ is 6-lower alkyl, 6-lower alkoxy or 6-halo of a different value from $R_5$.

32. A method as claimed in claim 31, wherein $R_1$ and $R_2$ are methyl.

33. A method as claimed in claim 31, wherein $R_4$ is hydrogen and $R_5$ is halo, lower alkyl or trifluoromethyl.

34. A method as claimed in claim 33, wherein $R_5$ is halo.

35. A method as claimed in claim 31, wherein $R_4$ is 6-lower alkoxy and $R_5$ is halo or lower alkoxy.

36. A method as claimed in claim 31, wherein $R_4$ is 6-halo and $R_5$ is lower alkoxy.

37. A method as claimed in claim 33, wherein $R_5$ is $C_1$-$C_4$ alkyl.

38. A therapeutic composition as claimed in claim 14, wherein $R_1$ and $R_2$ are methyl.

39. A therapeutic composition as claimed in claim 14, wherein $R_4$ is hydrogen and $R_5$ is halo, lower alkyl or trifluoromethyl.

40. A therapeutic composition as claimed in claim 39, wherein $R_5$ is halo.

41. A therapeutic composition as claimed in claim 14, wherein $R_4$ is 6-lower alkoxy and $R_5$ is halo or lower alkoxy.

42. A therapeutic composition as claimed in claim 14, wherein $R_4$ is 6-halo and $R_5$ is lower alkoxy.

43. A therapeutic composition as claimed in claim 42, wherein $R_5$ is $C_1$-$C_4$ alkyl.

* * * * *

UNITED STATES PATENT AND TRADEMARK OFFICE
CERTIFICATE OF CORRECTION

PATENT NO. : 4,302,460

DATED : November 24, 1981

INVENTOR(S) : Roy V. Davies, James Fraser, Kenneth J. Nichol, Raymond Parkinson, Malcolm F. Sim and David B. Yates It is certified that error appears in the above—identified patent and that said Letters Patent is hereby corrected as shown below:

[56] References Cited, OTHER PUBLICATIONS, eighth reference; "(1970)" should read -- (1978) -- original reference

[57] ABSTRACT, ninth line from bottom; delete "and $R_4$"

Col. 4, line 37; "quinolines" should read -- quinolones --

Col. 5, line 40; cancel "diastereoisomers" and insert -- enantiomers --

Col. 6, line 14; insert a period -- . -- after "carboxymethylcellulose"

Col. 8, line 7; insert a period -- . -- after "minutes"

Col. 11, line 42; insert -- (g) -- before "8-fluoro-"

Col. 12, approximately line 23 (in first part of Table, line 9); "4-OCOCH$_3$" should read -- 4-COCH$_3$ --

Col. 12, approximately line 24 (in first part of Table, line 10); "3-OCOCH$_3$" should read -- 3-COCH$_3$ --

Col. 14, line 18; "produce" should read -- product --

Col. 15, line 52; "residue" should read -- residual --

Col. 18, line 58; "$R_3R_4$" should read -- $R_3$, $R_4$ --

Col. 18, line 63; delete "is" (second occurrence)

Col. 5, line 39; cancel "diastereoisomeric" and insert -- enantiomeric --

Signed and Sealed this

Twenty-seventh Day of April 1982

|SEAL|

Attest:

GERALD J. MOSSINGHOFF

Attesting Officer — Commissioner of Patents and Trademarks